(12) United States Patent
Lee et al.

(10) Patent No.: US 7,150,853 B2
(45) Date of Patent: Dec. 19, 2006

(54) METHOD OF STERILIZING A MEDICAL DEVICE

(75) Inventors: Jeong S. Lee, Diamond Bar, CA (US); Kenneth L. Wantink, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 353 days.

(21) Appl. No.: 10/002,933

(22) Filed: Nov. 1, 2001

(65) Prior Publication Data

US 2003/0083616 A1 May 1, 2003

(51) Int. Cl.
*A61L 2/08* (2006.01)

(52) U.S. Cl. .......................................... 422/23; 422/22

(58) Field of Classification Search .................. 422/22, 422/23
See application file for complete search history.

(56) References Cited

U.S. PATENT DOCUMENTS

| | | | |
|---|---|---|---|
| 4,813,210 A | | 3/1989 | Masuda et al. |
| 5,444,103 A | * | 8/1995 | Tabata et al. .................. 522/5 |
| 5,554,120 A | | 9/1996 | Chen et al. .................... 604/96 |
| 5,556,383 A | | 9/1996 | Wang et al. ................... 604/96 |
| 5,728,748 A | * | 3/1998 | Sun et al. ...................... 522/65 |
| 5,733,496 A | * | 3/1998 | Avellanet .................... 264/470 |
| 5,849,846 A | * | 12/1998 | Chen et al. .................. 525/166 |
| 5,957,975 A | * | 9/1999 | Lafont et al. ................... 623/1 |
| 6,079,413 A | | 6/2000 | Baran |
| 6,203,551 B1 | * | 3/2001 | Wu ............................ 606/108 |

FOREIGN PATENT DOCUMENTS

| | | | |
|---|---|---|---|
| EP | 490472 A2 | * | 6/1992 |
| EP | 1 016 430 A1 | | 7/2000 |
| GB | 2180815 | | 4/1987 |
| JP | 404085340 A | * | 3/1992 |
| WO | WO 99/13924 A2 | * | 3/1999 |

\* cited by examiner

*Primary Examiner*—E. Leigh McKane
(74) *Attorney, Agent, or Firm*—Fulwider Patton LLP

(57) ABSTRACT

A method of sterilizing a medical device component, such as a catheter balloon, in which an electron beam (i.e., e-beam) is applied to the component in an evacuated or inert gas-filled container. The method of the invention allows for electron beam sterilization without significant degradation of the component polymeric material. In one embodiment, the device component is configured to be pressurized or expanded during use. The method of the invention provides a component with a rupture pressure that is not significantly decreased due to electron beam sterilization. Another aspect of the invention is a medical device component, e-beam sterilized according to a method of the invention. A variety of medical device components can be sterilized by the method of the invention, and particularly intracorporeal devices for therapeutic or diagnostic purposes, such as balloon catheters, catheter shafts and balloons, stent covers, and vascular grafts.

7 Claims, 2 Drawing Sheets

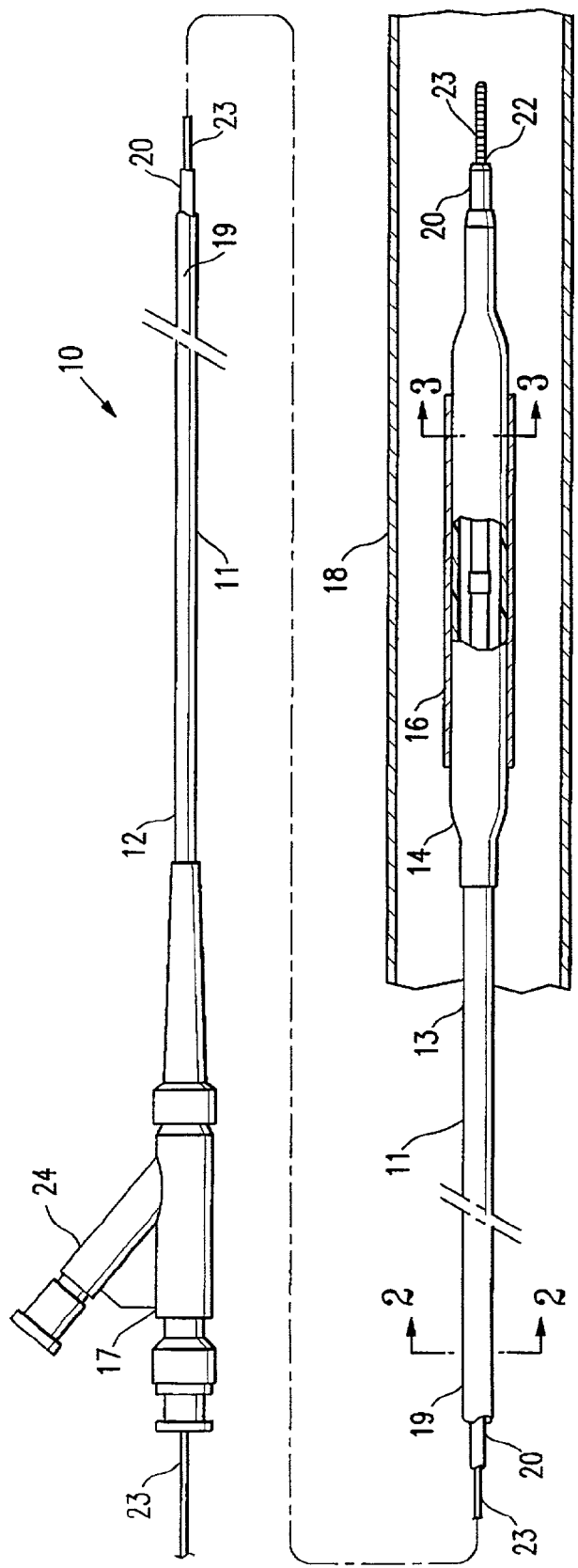

METHOD OF STERILIZING A MEDICAL DEVICE

BACKGROUND OF THE INVENTION

This invention relates generally to medical devices, and particularly to balloon catheters, including angioplasty and stent delivery balloon catheters.

In percutaneous transluminal coronary angioplasty (PTCA) procedures, a guiding catheter is advanced until the distal tip of the guiding catheter is seated in the ostium of a desired coronary artery. A guidewire, positioned within an inner lumen of a dilatation catheter, is first advanced out the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with liquid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. Substantial, uncontrolled expansion of the balloon against the vessel wall can cause trauma to the vessel wall. After the balloon is finally deflated, blood flow resumes through the dilated artery and the dilatation catheter can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant an intravascular prosthesis, generally called a stent, inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion.

In the design of catheter balloons, balloon characteristics such as strength, flexibility and compliance must be tailored to provide optimal performance for a particular application. Angioplasty balloons preferably have high strength and a high rupture pressure for inflation at relatively high pressure, and high flexibility and softness for improved ability of the catheter to track the tortuous anatomy and cross lesions. The balloon compliance is chosen so that the balloon will have a desired amount of expansion during inflation. Compliant balloons exhibit substantial stretching upon application of internal pressure, whereas noncompliant balloons exhibit relatively little stretching during inflation.

In the manufacture of catheter balloons, a variety of methods have been used to sterilize the catheter before use including exposure to an electron beam (i.e., e-beam) or a sterilizing fluid such as ethylene oxide (i.e., EtO). One difficulty has been sterilizing polymeric materials which degrade substantially in response to a conventional sterilization method. Degradation of the polymeric material will reduce the rupture pressure of the catheter balloon. Increasing the wall thickness of such balloons to provide an acceptably high rupture pressure increases the profile and stiffness of the balloon, and consequently decreases the trackability and crossability of the catheter in the patient's vasculature. Thus, what has been needed is an improved method of sterilizing medical devices.

SUMMARY OF THE INVENTION

This invention is directed to a method of sterilizing a medical device component, such as a catheter balloon or shaft, in which an electron beam (i.e., e-beam) is applied to the component in an evacuated or inert gas-filled container. The method of the invention allows for electron beam sterilization without significant degradation of the component polymeric material. It is believed that by minimizing the presence of air during the electron beam sterilization, the method inhibits or prevents the formation of reactive oxygen and nitrogen radicals which would otherwise form from the action of the electron beam radiation on air. Another aspect of the invention is a medical device component, e-beam sterilized according to a method of the invention. A variety of medical device components can be sterilized by the method of the invention, and particularly intracorporeal devices for therapeutic or diagnostic purposes, such as balloon catheters, catheter shafts and balloons, stent covers, and vascular grafts. In one embodiment, the device component is configured to be pressurized or expanded during use, and the method of the invention provides such a device component with a rupture pressure that is not significantly decreased due to electron beam sterilization. Although discussed primarily in terms of a balloon for a balloon catheter, the invention should be understood to include other medical devices. The terminology "medical device component" should be understood to include an independent, complete item such as a vascular graft or balloon catheter, or alternatively, a part of a larger device such as a balloon or a shaft of a balloon catheter.

In one embodiment, the balloon itself, which has typically already been secured to a catheter shaft to form an assembled balloon catheter, is evacuated and/or filled with an inert gas before the electron beam sterilization. In a presently preferred embodiment, the balloon is purged by applying a vacuum to evacuate the balloon and back filling the evacuated balloon with an inert gas. Thus, the air which would have been present inside the balloon and catheter shaft interior is removed and replaced with an inert gas before the electron beam sterilization. As a result, the degradation of the balloon polymeric material due to the electron beam sterilization is minimized. In a presently preferred embodiment, the balloon catheter is purged before being placed inside the container, and before the container is similarly purged by evacuating the container and back filling the container with an inert gas. However, in an alternative embodiment, the balloon catheter is purged after being placed in the container.

The inert gas used for purging in the method of the invention is a gas which when exposed to an electron beam does not form radicals causing oxidative degradation, i.e., hydrogen abstracting radicals. Preferred inert gases are noble gases, and most preferably argon. The heaviness of argon makes it more preferable than helium. However, gases other than the noble gases could be used as the inert gas, provided the gases lack oxygen. Thus, for example, nitrogen could be used as a low cost alternative to argon as the purging gas, because nitrogen is less susceptible than oxygen to the formation of reactive radicals causing oxidative degradation, upon exposure to an electron beam. Thus, the air tight, oxygen- or air-free container sealed with the balloon catheter therein provides an environment for the catheter during electron beam sterilization which does not form reactive radicals which cause significant oxidative degradation of the balloon catheter upon exposure to the electron beam during the sterilization.

In a presently preferred embodiment, the container is filled with inert gas so that the container has a positive pressure which thus prevents or inhibits air leaking into the container in the event that pinholes develop in the container. The inert gas consequently prevents degradation of the balloon polymer during or shortly after the electron beam application and the attendant loss of sterilization if pin holes develop in the container during storage of the catheter. However, in an alternative embodiment, the container is merely evacuated by applying a vacuum to the container and sealing the container, without necessarily filling the container with an inert gas before and the container sealed with the medical device component therein. The container and balloon are evacuated by applying a vacuum to an interior thereof to thereby reduce the internal pressure therein to less than the ambient pressure. For example, the absolute pressure in the evacuated container is typically not greater than about 50 mTorr. After filling with the inert gas, the pressure inside the inert gas-filled container is typically not less than about 1 atm (760 Torr). In a presently preferred embodiment, the container (with the balloon catheter therein) is purged inside a vacuum chamber. Thereafter, the container may be sealed inside the evacuated or inert gas-filled vacuum chamber if the vacuum chamber contains a sealer, or transferred to another vacuum chamber containing a sealer. Alternatively, the purged container may be removed from the vacuum chamber and maintained in an open end-up orientation and sealed outside the vacuum chamber. Inert gas such as argon is heavier than air and will thus prevent air going into the argon-filled container when the container is held with the open end of the container up in an air-filled environment prior to sealing the container.

A catheter polymeric balloon sterilized according to the method of the invention has minimal degradation of the polymer, and consequently, a minimal decrease in rupture pressure due to the sterilization. After the electron beam sterilization according to the method of the invention, the balloon has a mean rupture pressure which is not significantly less than (i.e., not more than 5% to about 25% less than, and preferably not more than about 10% to about 15% less than) the rupture pressure of the balloon before the electron beam sterilization of the method of the invention. Furthermore, the balloon preferably has a high fatigue resistance, i.e., cycles to failure, which is not significantly less than (i.e., not more than about 5% to about 10% less than) the fatigue resistance of the balloon before the electron beam sterilization of the method of the invention. After accelerated aging to simulate shelf life of the balloon in which the balloon is aged at about 45° C. to about 65° C. for about 1 to about 3 weeks, a balloon sterilized according to the method of the invention in an evacuated or inert gas-filled container has a mean rupture pressure which is significantly higher than (i.e., more than about 15% to about 25% higher than) the rupture pressure of a balloon electron beam sterilized in the presence of air although otherwise similarly aged and sterilized, and a fatigue resistance which is significantly higher than (i.e., more than about 1000% to about 1500% higher than) the fatigue resistance of the balloon electron beam sterilized in the presence of air.

The medical device component sterilized according to the method of the invention can be formed of a variety of suitable polymeric materials, and in one embodiment is formed of a polymeric material selected from the group consisting of polyamides and fluoropolymers. In a presently preferred embodiment, the balloon is formed of a polyamide polymeric material such as polyether block amides (PEBAX), available from Atochem. The PEBAX material would typically degrade as a result of an electron beam sterilization in the presence of air. Therefore, in one embodiment, the method of the invention provides an electron beam sterilized PEBAX balloon with a sufficiently high rupture pressure and fatigue resistance, and without requiring an increase in the balloon wall thickness to maintain the rupture pressure and fatigue resistance of the balloon. A catheter balloon of the invention typically has a wall thickness of about 0.0005 to about 0.001 inches (about 0.013 to about 0.03 mm) for a 3.0 mm nominal outer diameter balloon, and a wall thickness of about 0.0008 to about 0.0015 inches (about 0.02 to about 0.04 mm) for a 5.0 mm nominal outer diameter balloon. Similarly, other medical device components sterilized by the method of the invention may be formed of PEBAX or fluoropolymers. For example, in one embodiment, a fluoropolymer such as polytetrafluoroethylene (TEFLON) or polyvinylidiene fluoride (PVDF) forms the catheter shaft, or a layer such as an inner lubricious liner of the catheter shaft, and the method of the invention provides for electron beam sterilization of the shaft without significant degradation of the fluoropolymer. Expanded polytetrafluoroethylene (ePTFE) fluoropolymer will degrade to a lesser degree when electron beam sterilized in the absence of air/oxygen according to the method of the invention, than when electron beam sterilized in the presence of air.

A balloon catheter sterilized according to a method of the invention generally comprises an elongated shaft having a proximal end, a distal end, and an inflation lumen therein, with the balloon secured to a distal shaft section and having an interior in fluid communication with the inflation lumen. The balloon catheter can be used for a variety of applications including PTCA, peripheral angioplasty, stent delivery, and the like.

The sterilization method of the invention avoids significant degradation of the polymeric material of the medical device component, as a result of sterilizing the medical device component in an evacuated or inert gas-filled container. Consequently, the method provides a sterilized medical device component such as a catheter balloon having a sufficiently high rupture pressure, without requiring an increase in the wall thickness of the balloon. The method thus provides for improved manufacturability of the balloon catheter, and a balloon catheter having excellent performance characteristics such as low profile and flexibility, for excellent trackability, and a desired rupture pressure and fatigue resistance. These and other advantages of the invention will become more apparent from the following detailed description and accompanying exemplary drawings.

BRIEF DESCRIPTION OF THE DRAWINGS

FIG. 1 is an elevational view, partially in section, of a balloon catheter for delivering a stent, having a balloon sterilized according to a method that embodies features of the invention.

FIG. 2 is a transverse cross-section of the catheter shown in FIG. 1, taken at line 2—2.

FIG. 3 is a transverse cross-section of the catheter shown in FIG. 1, taken at line 3—3.

DETAILED DESCRIPTION OF THE INVENTION

Figure 4:
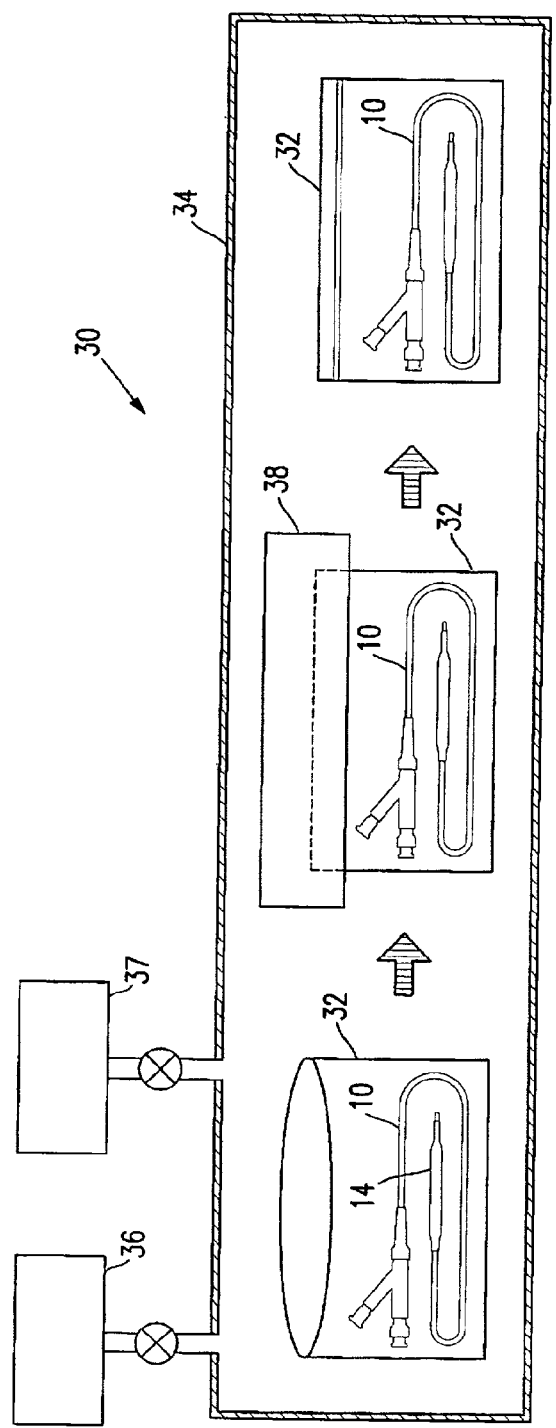
FIG. 4 illustrates a balloon catheter in a container during electron beam sterilization according to a method which embodies features of the invention.

FIG. 1 illustrates an over-the-wire type stent delivery balloon catheter 10 embodying features of the invention. Catheter 10 generally comprises an elongated catheter shaft 11 having a proximal end 12, a distal end 13, and an inflatable balloon 14 on a distal shaft section. An expandable stent 16 is mounted on balloon 14 for implanting in the patient's body lumen 18. In the embodiment illustrated in FIG. 1, the shaft 11 comprises an outer tubular member 19 and an inner tubular member 20. As best shown in FIGS. 2 and 3, illustrating transverse cross sections of the catheter 10 shown in FIG. 1, taken along lines 2—2 and 3—3, respectively, outer tubular member 19 defines an inflation lumen 21, and inner tubular member 20 disposed within the outer tubular member lumen 21 defines a guidewire lumen 22 configured to slidingly receive a guidewire 23. Inflatable balloon 14 is disposed on a distal section of catheter shaft 12, having a proximal end sealingly secured to the distal end of outer tubular member 19 and a distal end sealingly secured to the distal end of inner tubular member 20, so that its interior is in fluid communication with inflation lumen 21. An adapter 24 at the proximal end of catheter shaft 11 is configured to provide access to guidewire lumen 22 and to direct inflation fluid through arm 26 into inflation lumen 21. The distal end of catheter may be advanced to a desired region of a patient's body lumen 18 in a conventional manner and balloon 14 inflated to expand stent 16. The catheter 10 is withdrawn after deflating the balloon 14, leaving the implanted stent 16 in the body lumen 18.

Balloon 14 is sterilized by applying an electron beam to the balloon 14 according to a method of the invention. FIG. 4 illustrates a schematic view of an apparatus 30 useful in a method which embodies features of the invention, with catheter 10 inside the apparatus 30. The catheter 10 is inside an open, sealable container 32 which is inside a vacuum chamber 34. Vacuum source 36 and inert gas source 37 are connected to the chamber 34, for evacuating chamber 34 and open container 32 therein and filling with an inert gas, respectively. In a presently preferred embodiment, the assembled catheter 10 with balloon 14 on catheter shaft 11 is purged before it is placed inside the chamber 34 or inside the container 32, by applying a vacuum to the inside of the catheter 10 and then filling the evacuated catheter 10 with inert gas. Specifically, the catheter is evacuated by reducing the absolute internal pressure therein to about 20 to about 250 mTorr, preferably about 20 to about 100 mTorr. The evacuated balloon is then filled with inert gas until the pressure inside the catheter is about 1 atm (760 Torr).

The purged catheter 10 is then placed inside the container 32 inside the chamber 34. Before the catheter 10 is placed inside the container 32, the balloon 14 is typically folded and pressed on the catheter shaft 11 under vacuum or inert gas, and if intended for use as a stent delivery catheter, the stent mounted on the balloon. The chamber 34 is then purged by evacuating and filling with an inert gas, which also purges the open container 32 therein. Specifically, the container 32 and chamber 34 are evacuated by reducing the pressure to a pressure of about 20 to about 250 mtorr, preferably about 20 to about 100 mTorr using vacuum source 36, and then filled with inert gas using inert gas source 37 to an absolute internal pressure of about 1 atm (760 Torr). The purged container 32 is then sealed with the catheter 10 therein. In the embodiment illustrated in FIG. 4, a bag sealer 38 is provided inside the chamber 34 for sealing the container 32 inside the chamber 34. However, in alternative embodiments (not shown), the bag sealer may be in a separate vacuum chamber or outside a vacuum chamber. Commercially available bag sealers may be used such as the AmeriVacs model AVC-20 bag sealer.

Although discussed in terms of purging by back-filling with an inert gas after being evacuated, in an alternative embodiment, the container 32 and/or catheter 10 may be merely evacuated by applying a vacuum without subsequently back-filling with inert gas before exposure to the electron beam. A variety of suitable inert gases may be used including the noble gases, and preferably argon, neon, xenon, and helium. The same inert gas is typically used to purge the balloon catheter 10, container 32, and chamber 34, although alternatively, different gases can be used.

After the purged and sealed container 32 with the catheter 10 therein is removed from the chamber 34, an electron beam from an electron beam source (not shown) is applied to at least the balloon 14 in the container 34, and typically to the entire catheter 10. A variety of suitable electron beam sources may be used, such as the Titan Scan available from Titan Ind., of San Diego. The electron beam is preferably applied to the catheter 10 by directing the beam toward and through the catheter, and traversing the beam or the catheter relative to oneanother to expose the entire length. In a presently preferred embodiment, the energy of the electron beam is about 3 to about 10 megarads (MRads). The electron beam can be applied to balloon 14 in a single dose of about 3 to about 10 MRads for about 2 to about 10 seconds, or alternatively, in multiple doses, each dose being about 2 to about 5 MRads lasting about 2 to about 10 seconds. Selection of the energy level of the electron beam, and the number and duration of doses will vary depending on factors including the packaging material, wall thickness, balloon polymeric material, and desired rupture pressure of the balloon, and are chosen such that sterilization is complete. The balloon 14 has a first mean rupture pressure before the electron beam is applied, and a second mean rupture pressure after the electron beam is applied which is equal to or not significantly less than the first rupture pressure. In one embodiment, the second rupture pressure is at least about 15 to about 25 atm. The electron beam energy level is preferably sufficient to sterilize the balloon 14 without causing significant degradation of the material of the balloon 14 or container 32 when the sterilization is performed according to the method of the invention with the balloon sealed inside the evacuated or inert gas-filled container.

For example, a 3.0 nominal outer diameter balloon formed of a polyether block amide blend, having a wall thickness of about 0.015 to about 0.030 mm, and specifically about 0.015 to about 0.025 mm, which has been sterilized according to the method of the invention in an evacuated and argon back-filled container by applying the electron beam in two doses of about 5 seconds per dose, at an energy level of 2.5 MRads, has a mean rupture pressure of at least about 15 to about 20 atm, and specifically of about 17 to about 20 atm. The rupture pressure of the balloon before the electron beam sterilization in the argon back-filled container (i.e., the first rupture pressure) is about 20 atm, so that the second rupture pressure is not more than about 15 to about 25 percent less than the first rupture pressure. In contrast, the rupture pressure of the balloon after electron beam sterilization in the presence of air is about 14 atm. The loss in mean rupture pressure may be even less with different grades of PEBAX.

In a presently preferred embodiment, container 32 is a plastic and/or foil pouch which can be sealed to be air tight. The container 32 is typically multilayered, with an outer layer of a polyester material, and an inner layer of a linear low density polyethylene material, and a foil layer between the inner and outer layers. The container 32 has a wall thickness of about 0.1 to about 0.15 mm, and a size configured to receive the catheter 10 or other medical device component and to be useful for transport and storage of the sterilized catheter 10 before use thereof.

In the embodiment illustrated in FIG. 1, stent 16 is mounted on an outer surface of balloon 14, for delivery and expansion within body lumen 18. A variety of suitable conventional stents can be used, which generally comprise metal struts formed of wire or a slotted tube configured to be expandable from a contracted configuration on the balloon to an expanded configuration (see for example U.S. Pat. No. 5,514,154 (Lau et al.), incorporated by reference herein in its entirety). In one embodiment, the balloon 14 is electron beam sterilized with stent 16 mounted on the outer surface of the balloon 14. As a result, the stent reduces the penetration of the electron beam into the sections of the balloon located directly underneath the stent (i.e., the sections of the balloon underneath the stent struts as opposed to the sections of the balloon located at the spaces in the stent wall between adjacent, spaced apart struts). By reducing the penetration of the electron beam, the stent 16 further minimizes the degradation of the balloon polymeric material due to the electron beam sterilization.

Figure 6:
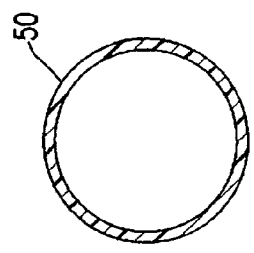
FIG. 6 is a transverse cross-section of the stent cover or vascular graft shown in FIG. 5, taken at line 6—6.
Figure 5:
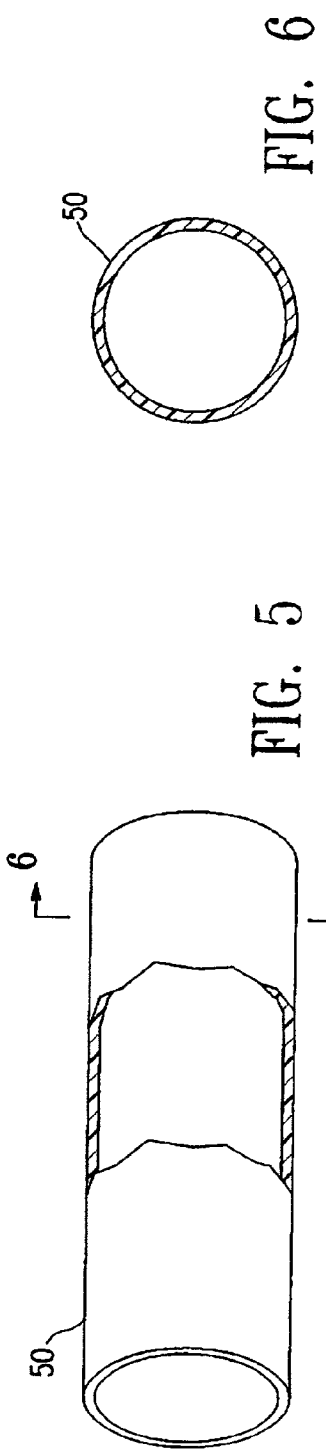
FIG. 5 illustrates a stent cover or vascular graft sterilized according to a method that embodies features of the invention.

The method of the invention can be used on a variety of polymeric medical device components including stent covers and vascular grafts. FIG. 5 illustrates an elevational, partially in section view of a stent cover or vascular graft 50, generally comprising a tubular, expandable body. FIG. 6 illustrates a transverse cross sectional view of the stent cover or vascular graft 50 shown in FIG. 5, taken along line 6—6. Stent cover 50 is configured to be mounted on an inner or outer surface of stent 16 and expanded therewith, as is conventionally known.

The dimensions of catheter 10 are determined largely by the size of the balloon and guidewires to be employed, catheter type, and the size of the artery or other body lumen through which the catheter must pass or the size of the stent being delivered. Typically, the outer tubular member 19 has an outer diameter of about 0.025 to about 0.04 inch (0.064 to 0.10 cm), usually about 0.037 inch (0.094 cm), and a wall thickness of about 0.002 to about 0.008 inch (0.0051 to 0.02 cm), typically about 0.003 to 0.005 inch (0.0076 to 0.013 cm). The inner tubular member 20 typically has an inner diameter of about 0.01 to about 0.018 inch (0.025 to 0.046 cm), usually about 0.016 inch (0.04 cm), and wall thickness of about 0.004 to about 0.008 inch (0.01 to 0.02 cm). The working length of the catheter 10 may range from about 90 to about 150 cm, and is typically about 143 cm. Balloon 14 has a length about 0.5 cm to about 4 cm and typically about 2 cm, and an inflated working diameter of about 1 to about 8 mm.

While the present invention is described herein in terms of certain preferred embodiments, those skilled in the art will recognize that various modifications and improvements may be made to the invention without departing from the scope thereof. For example, in the embodiment illustrated in FIG. 1, the catheter is over-the-wire stent delivery catheter. However, one of skill in the art will readily recognize that other types of intravascular catheters may be used, such as rapid exchange dilatation catheters having a distal guidewire port and a proximal guidewire port and a short guidewire lumen extending between the proximal and distal guidewire ports in a distal section of the catheter. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed is:

1. A method of sterilizing a balloon of a balloon catheter, comprising
   a) providing a balloon catheter having a balloon with a first rupture pressure; and
   b) applying an electron beam to the balloon catheter in an evacuated or inert gas-filled container, so that the electron-beamed balloon has a second rupture pressure equal to or less than the first rupture pressure, the second rupture pressure being not more than about 15% to about 25% less than the first rupture pressure.

2. The method of claim 1 including purging the container with the balloon catheter therein by evacuating the container and filling the evacuated container with inert gas, and sealing the purged container with the balloon catheter therein, before the electron beam is applied.

3. The method of claim 2 including purging the balloon catheter by evacuating the balloon catheter and filling with inert gas, before the container sealed.

4. The method of claim 3 wherein the balloon catheter is purged before being placed in the container and before the container is purged.

5. The method of claim 3 wherein the container is purged inside an evacuated or inert gas-filled chamber.

6. The method of claim 3 wherein the purged container is sealed inside the evacuated or inert gas-filled chamber.

7. The method of claim 2 including mounting a stent on an outer surface of the balloon before the electron beam is applied, and the electron beam is applied to the outer surface of the balloon so that the stent reduces penetration of the electron beam into sections of the balloon located directly underneath the stent.

* * * * *